United States Patent [19]

Kost et al.

[11] Patent Number: 4,948,587
[45] Date of Patent: Aug. 14, 1990

[54] ULTRASOUND ENHANCEMENT OF TRANSBUCCAL DRUG DELIVERY

[75] Inventors: Joseph Kost, Omer, Israel; Robert S. Langer, Somerville, Mass.

[73] Assignee: Massachusetts Institute of Technology, Cambridge, Mass.

[21] Appl. No.: 233,590

[22] Filed: Aug. 18, 1988

Related U.S. Application Data

[60] Continuation-in-part of Ser. No. 883,111, Jul. 8, 1986, Pat. No. 4,767,402, and Ser. No. 936,000, Nov. 28, 1986, which is a division of Ser. No. 633,366, Jul. 23, 1984, Pat. No. 4,657,543.

[51] Int. Cl.$^5$ .............................................. A61F 13/00
[52] U.S. Cl. ..................................... 424/435; 424/434
[58] Field of Search ............. 424/434, 435; 128/24 A; 604/22

[56] References Cited

U.S. PATENT DOCUMENTS

| | | | |
|---|---|---|---|
| 4,127,125 | 11/1978 | Takemoto et al. | 128/172.1 |
| 4,176,664 | 12/1979 | Kalish | 128/256 |
| 4,280,494 | 7/1981 | Cosgrove et al. | 128/213 R |
| 4,309,989 | 1/1982 | Fahim | 424/642 X |
| 4,372,296 | 2/1983 | Fahim | 424/642 X |
| 4,563,184 | 1/1986 | Korol | 604/368 |
| 4,780,212 | 10/1988 | Kost et al. | 210/652 X |

OTHER PUBLICATIONS

Robinson and Lee, Controlled Drug Delivery, pp. 42–43.
Skauen & Zentner, "Phonophoresis", Int. J. Pharm. 20, 235–45 (1984).
Ebert et al., Controlled Release Technology Pharmaceutical *Applications* 23, 320–21, Lee & Good eds., (Am. Chem. Soc. 1987).
Eggert et al., *Proceed. Intern. Sympo. Control. Rel. Bioact. Mater.* 14, 180–81 (1987).
Lee et al., *Proceed. Intern. Symp. Control. Rel. Bioact. Mater.* 14, 55–56 (1987).
Lee & Rashi, *Proceed. Intern. Symp. Control. Rel. Bioact. Mater.* 14, 53–54 (1987).
Olanoff & Gibson, *Controlled Release Technology Pharmaceutical Application* 22, 301–309, Lee & Good, eds. (American Chem. Soc. '87).
Wheatley et al., *Proceed. Intern. Symp. Control. Rel. Bioact. Mater.* 14, 26–27 (1987).
Veillard et al., *Proceed. Intern. Symp. Control. Rel. Bioact. Mater.* 14, 22 (1987).

*Primary Examiner*—Thurman K. Page
*Attorney, Agent, or Firm*—Kilpatrick & Cody

[57] ABSTRACT

A method using ultrasound for enhancing and controlling transbuccal permeation of a molecule, including drugs, antigens, vitamins, inorganic and organic compounds, and various combinations of these substances, through the buccal membranes and into the circulatory system. The frequency and intensity of ultrasonic energy which is applied, and the length of time of exposure are determined according to the location and nature of the buccal membrane and the substance to be infused. Levels of the infused molecules in the blood and urine measured over a period of time are initially used to determine under what conditions optimum transfer occurs. In a variation of the method, whereby ultrasound is applied directly to the compound and site where the compound is to be infused through the buccal membranes, the compound can be placed within a delivery device. In one variation, the ultrasound can control release both by direct interaction with the compound and membrane but also with the delivery device. In another variation, the delivery device helps to modulate release and infusion rate. The compound can also be administered in combination with a chemical agent which alters permeability of the buccal membrane, thereby aiding infusion of the compound into the circulatory system.

18 Claims, No Drawings

ULTRASOUND ENHANCEMENT OF TRANSBUCCAL DRUG DELIVERY

BACKGROUND OF THE INVENTION

The U.S. Government has certain rights in this invention by virtue of National Institute of Health Grant No. NIH-2R04-GM26698-07.

This application is a continuation-in-part of U.S. Ser. No. 883,111 entitled 'Ultrasound Enhancement of Transdermal Drug Delivery" filed July 8, 1986 by Joseph Kost and Robert S. Langer, issued Aug. 30, 1988 as U.S. Pat. No. 4,767,402, and U.S. Ser. No. 936,000 entitled "Ultrasonically Modulated Polymeric Devices for Delivering Compositions" filed Nov. 28, 1986 by Joseph Kost and Robert S. Langer, which is a divisional of U.S. Ser. No. 633,366 filed July 23, 1984, issued April 14, 1987 as U.S. Pat. No. 4,657,543.

Drugs are routinely administered either orally or by injection. The effectiveness of most drugs is dependent on achieving a certain concentration in the bloodstream. Although some drugs have inherent side effects which cannot be eliminated in any dosage form, many drugs exhibit undesirable effects that are specifically related to a particular route of administration. For example, drugs may be degraded in the gastrointestinal tract by the low gastric pH, local enzymes or interaction with food or drink within the stomach. The drug or disease itself may forestall or compromise drug absorption because of vomiting or diarrhea. If a drug survives its trip through the gastrointestinal tract, it may face rapid metabolism to pharmacologically inactive forms by the liver, the first-pass effect. Sometimes the drug itself has inherent undesirable attributes such as a short half-life, high potency or a narrow therapeutic blood level range.

Some of the recent efforts aimed at eliminating some of the problems of traditional dosage forms have involved transdermal delivery of the drugs. Topical application has been used for a very long time, mostly in the treatment of localized skin diseases. Local treatment, however, only requires that the drug permeate the outer layers of the skin to treat the diseased state, with little or no systemic accumulation. Transdermal delivery systems are specifically designed to obtain systemic blood levels. Transdermal permeation or percutaneous absorption can be defined as the passage of a substance, such as a drug, from the outside of the skin through its various layers into the bloodstream.

The transport of drugs through the skin is complex since many factors influence their permeation. These include the skin structure and its properties, the penetrating molecule and its physical-chemical relationship to the skin and the delivery matrix, and the combination of the skin, the penetrant, and the delivery system as a whole. Topical application of drugs has focused much attention on skin permeability properties. Many reports have described efforts to change skin permeability using chemical enhancers, molecules which enter the stratum corneum and decrease its resistance to drug penetration, or by external means such as iontophoresis. Chemical agents such as dimethylsulfoxide (DMSO), or 1-dodecylazacycloheptan-2-one (Azone), tend to enhance the penetration of drugs that are incorporated within them. However, other than in methods utilizing ultrasound, as described in U.S. Ser. No. 883,111 entitled "Ultrasound Enhancement of Transdermal Drug Delivery" filed July 8, 1986 by Joseph Kost and Robert S. Langer, and iontophoresis, there is no way of externally controlling the rate of drug release.

Buccal administration potentially offers certain advantages for delivery of drugs which cannot be easily or efficaciously administered by other routes such as oral or intravenous routes. However, as described by Ebert, et al., in Ch. 23. Transbuccal Absorption of Diclofenac Sodium in a Dog Model, *Controlled Release Technology Pharmaceutical Application,* ed. Ping I. Lee and William R. Good, 310–321 (American Chemical Society 1987), transbuccal drug delivery has received relatively little attention and few well-controlled studies of buccal mucosa permeability have been conducted.

The oral mucosa provides a protective coating for underlying tissues while acting as a barrier to microorganisms and as a control to the passage of substances through the oral cavity. In humans, the buccal membranes consist of keratinized and nonkeratinized striated epithelium. Many factors, including partition characteristics, degree of ionization, and molecular size, influence the transport of drugs across the membrane. Many drugs do not pass through the buccal membranes in sufficient amounts to be useful. Insulin is a primary example of a drug which is very poorly absorbed through the buccal membranes and which also cannot be given orally due to degradation and poor absorption in the gastrointestinal tract.

The few previous attempts to enhance buccal membrane permeability have followed the studies on enhancing intranasal delivery, using agents which increase permeability, such as histamine and other vasoactive compounds, and surfactants, such as hydrophobic bile salt derivatives, described by Olanoff, et al., in Ch. 22 Method to Enhance Intranasal Peptide Delivery *Controlled Release Technology Pharmaceutical Application,* ed. Ping I. Lee and William R. Good, 301–309 (American Chemical Society 1987). It is obvious that these methods are not easily utilized within the mouth.

It is therefore an object of the present invention to provide a method for enhancing and controlling permeation of a molecule through the buccal membranes and into the circulatory system.

It is a further object of the invention to provide a method for enhancing permeation through the buccal membranes which is non-invasive and does not harm either the membrane or the molecules being infused.

It is still another object of the invention to provide an improved method for transbuccal delivery of drugs where the primary goal is to achieve a suitable therapeutic blood level at a rate independent of the drug being infused.

It is a further object of the present invention to provide an improved method for transbuccal delivery of a drug which is useful with a variety of molecules, including molecules soluble in a aqueous, inorganic or lipid solution.

It is still another object of the present invention to provide a simple, efficient, reproducible and economical method for enhancing transbuccal permeation.

SUMMARY OF THE INVENTION

The present invention is a method using ultrasound for enhancing and controlling transbuccal permeation of a molecule, including drugs, antigens, vitamins, inorganic and organic compounds, and various combinations of these substances, through the buccal membranes and into the circulatory system. The frequency and intensity of ultrasonic energy which is applied, and the length of time of exposure are determined according to the location and nature of the buccal membrane and the substance to be infused. Levels of the infused molecules in the blood and urine measured over a period of time are initially used to determine under what conditions optimum transfer occurs.

In general, the frequency range of the ultrasound is between 20 kHz and 10 MHz, with intensities between 0 and 4 W/cm$^2$. Intensity is decreased as the frequency is decreased to prevent damage to the buccal membranes. The preferred range of frequencies is between 0.5 MHz and 1.5 MHz and the preferred range of intensities is between 2 and 4 W/cm$^2$. Exposure is for up to 10 minutes for most medical uses. The ultrasound may be pulsed or continuous. The frequency, intensity and time of exposure are interdependent as well as a function of the molecule being diffused and the nature of the membrane at the site of exposure. One way of determining the maximum limit of exposure is to measure membrane temperature, decreasing or stopping the treatment when the temperature of the skin rises one to two degrees Centigrade.

In a variation of the method whereby ultrasound is applied directly to the compound and site where the compound is to be infused through the buccal membranes, the compound can be placed within a delivery device, for example, similar to a small transdermal patch, or microencapsulated, so that the ultrasound can control release both by direct interaction with the compund and membrane but also with the delivery device.

DETAILED DESCRIPTION OF THE INVENTION

The present invention is a method for controlling and enhancing the rate and efficacy of permeation of a drug through buccal membranes into the circulatory system which utilizes a limited exposure of the infusion site to ultrasound. The ultrasound alters the passage of the molecules through the epithelial cells, via intercellular and intracellular penetration. The required length of time and frequency and intensity of ultrasound exposure are dependent on a number of factors including membrane thickness and resistance to permeation, which varies from species to species.

Ultrasound is sound having a frequency greater than about 20 kHz. Ultrasound used for medical diagnostic purposes usually employs frequencies ranging from 1.6 to about 10 MHz. As disclosed here, frequencies of between 20 kHz and 10 MHz with intensities between 0 and 4 W/cm$^2$, preferably between 2 and 4 W/cm$^2$, are used to enhance transbuccal transfer of molecules, although this range is variable according to the species, molecule and site of infusion, and may be expanded after testing to determine optimum parameters to achieve the desired levels while minimizing damage to the infusion site. The preferred frequency range is between 0.5 MHz and 1.5 W/cm$^2$. Compounds which alter the permeability of the buccal membranes, such as some of the compounds known to those skilled in the art and referred to in Olanoff, et al., in Ch. 22 Method to Enhance Intranasal Peptide Delivery *Controlled Release Technology Pharmaceutical Application,* ed. Ping I. Lee and William R. Good, 301–309 (American Chemical Society 1987), can also be utilized in conjunction with the ultrasound to alter the required frequency and intensity and time required to achieve the desired infusion of compound. Devices are available which emit both pulsed and continuous ultrasound. Exposures of only a few minutes are usually sufficient since the response time to the ultrasound is very rapid. Care must be taken to avoid excessive exposure which might cause burning. The temperature of the membrane is one indicator of overexposure. In the present invention as applied to humans, the temperature is held under 38° C.

The specific embodiment of the ultrasound device is not crucial. Probes, baths and boxes are all useful depending on where the ultrasound is to be applied. A number of devices are commercially available.

In contrast to the disclosure in U.S. Ser. No. 883,111 entitled "Ultrasound Enhancement of Transdermal Drug Delivery" filed July 8, 1986 by Joseph Kost and Robert S. Langer, a liquid media between the ultrasound applicator and the membrane is not essential due to the high level of moisture which is normally present at the surface of the buccal membranes. Optionally, any type of aqueous or inorganic gel which is non-toxic and preferably not unpleasant tasting and having an absorption coefficient similar to that of water may be used as the medium between the buccal membranes and the ultrasound applicator.

In a variation of the method wherein ultrasound is applied directly to the compound and site where the compound is to be infused into or through the buccal membranes, the compound can be located within a delivery device for additional rate control. The device can be polymeric or similar to the transdermal patches presently in use. The material can be sensitive to the ultrasound, as described in U.S. Ser. No. 936,000 entitled "Ultrasonically Modulated Polymeric Devices for Delivering Compositions" filed Nov. 28, 1986 by Joseph Kost and Robert S. Langer, or release compound at a rate independent of the application of ultrasound. Many formulations are known to those skilled in the art which are safe for use internally and dissolve in the mouth. Many biocompatible polymers can be used to form a polymeric matrix for the compound to be delivered, including both biodegadable and non-biodegradable polymers such as polyanhydrides, polylactic acid, polyglycolic acid, ethylene vinyl acetate copolymers, polypropylene, polyethylene. The release rate can also be manipulated by the form used to encapsulate the compound to be delivered. For example, the release rate from microcapsules is different from a slab containing compound, even when made of the same material.

The advantage of using ultrasound is that the rate and efficiency of transfer is both improved and controlled. Drugs which would simply not pass through the buccal membranes and into the circulatory system, or pass at a rate which is inadequate or variable over time, are forced through the epithelial cells of the membrane when ultrasound is applied. By controlling the frequency, intensity and time of exposure, the rate of transfer is controlled. Measurements taken over time of the blood or urine concentrations can be used to determine at what point the ultrasound conditions are correct.

In the preferred embodiment, ultrasound is used to enhance the passage of a compound through the membrane of a patient. Greater control and drug utilization is achieved by increasing the rate and directional control of the applied drug. The percentage of drug which quickly enters the bloodstream is increased accordingly and undesirable side effects avoided. The application of ultrasound allows transbuccal infusion of drugs which would otherwise not be possible. The goal is to infuse molecules through the buccal membranes into the bloodstream at an optimal rate. In the transdermal devices or "patches" presently in use, even drugs with low molecular weights such as nitroglycerin take 30 minutes to enter the bloodstream. A hypertension drug such as Catapresan may take up to two days to fully enter the bloodstream. It is highly desirable to decrease the rate of entry of these drugs to a matter of a few minutes, less than the time required for the drug to enter the bloodstream when given orally and absorbed through the gastrointestinal tract.

Examples of drugs which may be administered using ultrasound to enhance and control infusion through the transbuccal membranes include biologically active peptides such as insulin, vasopressin, enkephalin, calcitonin, nitroglycerin, compounds which do not easily diffuse into the bloodstream due to large molecular weight, hydrophobicity, or other factors, and compounds which are degraded in the gastrointestinal tract.

Although this invention has been described with reference to specific embodiments, it is understood that modifications and variations of the method for using ultrasound energy to enhance passage of molecules into and through skin may occur to those skilled in the art. It is intended that all such modifications and variations be included within the scope of the appended claims.

We claim:

1. A method for enhancing and controlling transbuccal infusion of molecules comprising:
   (a) selecting the molecules to be infused through the buccal membranes;
   (b) applying said molecules to the buccal membrane;
   (c) applying ultrasound to said molecules at a frequency of between 20 kHz and 10 MHz and an intensity of between 0 and 4 W/cm$^2$; and
   (d) varying the frequency and intensity over time to infuse said molecules through the transbuccal membranes at an optimal rate into the circulatory system without delay or damaging the buccal membranes, wherein the optimal rate is determined by measurements of a physiological fluid.

2. The method of claim 1 further comprising measuring the concentration of said molecules in a physiological fluid during or immediately after administration of the ultrasound.

3. The method of claim 1 further comprising measuring the concentrations of said molecule in the physiological fluid over time, determining the rate of transbuccal transfer for said molecules at specific frequencies, intensities and times of ultrasound application, wherein the molecules are subsequently infused using ultrasound at the frequency, intensity, and time of application determined to yield a specific concentration.

4. The method of claim 1 wherein the ultrasound frequency is applied at between 0.5 MHz and 1.5 MHz and an intensity of between 2 and 4 W/cm$^2$.

5. The method of claim 1 wherein the ultrasound is applied for less than ten minutes.

6. The method of claim 1 wherein the ultrasound is pulsed.

7. The method of claim 1 wherein the ultrasound is continuous.

8. The method of claim 1 wherein the molecule is selected from the group of molecules consisting of proteins, drugs, antigens, vitamins, inorganic compounds, organic compounds, and combinations thereof, wherein said molecule has a biological effect when infused into the circulatory system.

9. The method of claim 1 further comprising measuring the temperature of the membrane where the ultrasound is applied and applying the ultrasound at a frequency and intensity over a period of time which does not cause an increase in skin temperature of more than 2° C.

10. A combination of molecules for transbuccal infusion and an ultrasound emitter adapted to enhance such infusion, the ultrasound emitter comprising control circuits adapted to deliver ultrasound at a frequency of between 20 kHz and 10 MHz and at an intensity of between 0 and 4 W/cm$^2$ for a period such that the molecules are infused through the buccal membrane at a controlled rate without damaging the membrane.

11. The combination of claim 10 further comprising means to measure the temperature of the buccal membrane at the infusion site.

12. A composition for controlled delivery through the buccal membranes comprising
   molecules in a pharmaceutically effective concentration in a medium suitable for administration through the buccal membranes when ultrasound is applied to said molecules at a frequency of between 20 kHz and 10 MHz and an intensity of between 0 and 4 W/cm$^2$.

13. The composition of claim 12 wherein said medium is a polymeric matrix and said molecules can diffuse out of said polymeric matrix into the buccal membranes.

14. The composition of claim 12 wherein said medium dissolves in the environment of the buccal membranes.

15. The composition of claim 12 wherein said medium is a polymeric matrix and said polymeric matrix releases said molecules from said matrix in a controlled manner over a specific time period when said matrix is exposed to ultrasonic energy.

16. The composition of claim 12 wherein said medium is a polymeric matrix formed of polymer selected from the group consisting of polyanhydrides, polylactic acid, polyglycolic acid, ethylene vinyl acetate copolymers, polypropylene, polyethylene, and other biocompatible polymers.

17. The composition of claim 12 further comprising chemical compounds which alter the permeability of the buccal membranes.

18. The composition of claim 12 further comprising a medium having an absorbtion coefficient similar to that of water which facilitates transfer of the ultrasound to the infusion site on the buccal membranes.

* * * * *